United States Patent
Trammel, II et al.

(10) Patent No.: US 7,449,332 B2
(45) Date of Patent: Nov. 11, 2008

(54) FLUID CONTAINMENT FOR LABORATORY CONTAINERS

(75) Inventors: Harold W. Trammel, II, Raleigh, NC (US); John P. Hall, Raleigh, NC (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 753 days.

(21) Appl. No.: 10/812,623

(22) Filed: Mar. 30, 2004

(65) Prior Publication Data

US 2004/0219665 A1 Nov. 4, 2004

Related U.S. Application Data

(60) Provisional application No. 60/458,925, filed on Mar. 31, 2003.

(51) Int. Cl.
*C12M 1/22* (2006.01)
*B01L 3/00* (2006.01)
*B65D 25/00* (2006.01)

(52) U.S. Cl. .......... 435/305.1; 435/305.4; 422/102; 220/698; 220/719; 220/731

(58) Field of Classification Search .......... 435/305.1, 435/305.4; 220/570, 698, 719, 731
See application file for complete search history.

(56) References Cited

U.S. PATENT DOCUMENTS

| | | | |
|---|---|---|---|
| 2,614,406 A | 10/1952 | Carpenter | |
| 2,753,049 A | 7/1956 | Gaines et al. | |
| 2,999,559 A | 9/1961 | Boyer | |
| 3,185,341 A | 5/1965 | Barbour | |
| 3,309,000 A | 3/1967 | Haverstick | |
| 3,836,041 A | 9/1974 | Allgeyer | |
| 4,038,149 A | 7/1977 | Liner et al. | |
| 4,163,374 A | 8/1979 | Moore et al. | |
| 4,316,560 A | 2/1982 | Carter | |
| 4,448,345 A | 5/1984 | Helms | |
| 4,598,050 A | 7/1986 | Brown | |
| 4,619,373 A | 10/1986 | Galer | |
| 4,839,280 A | 6/1989 | Banes | |
| 4,900,160 A | 2/1990 | Brooks et al. | |
| 4,907,714 A | 3/1990 | Gatz | |
| 4,940,158 A | 7/1990 | Farrell et al. | |
| 5,122,470 A | 6/1992 | Banes | |
| 5,137,188 A | 8/1992 | Thompson | |

(Continued)

FOREIGN PATENT DOCUMENTS

WO    WO 03/014289 A3    2/2003

*Primary Examiner*—William H Beisner
(74) *Attorney, Agent, or Firm*—Nanette S. Thomas

(57) ABSTRACT

A culture dish assembly includes a polygonal culture dish with a bottom wall and a side wall enclosure formed by a plurality of generally planar panels joined consecutively to one another by non-planar corners. The side wall enclosure includes a generally planar top edge. Inner surface regions of a plurality of the planar panels are formed with a plurality of projections or recesses that are spaced from one another and spaced from the corners. A splash guard includes engagement flanges disposed for nesting with inner peripheral surface regions of the panels of the side wall enclosure. The engagement flanges include projections or recesses disposed for releasably engaging the projections or recesses on the side wall enclosure to hold the splash guard on the culture dish without creating stress concentrations in the corners.

10 Claims, 16 Drawing Sheets

U.S. PATENT DOCUMENTS

| | | |
|---|---|---|
| 5,213,239 A | 5/1993 | Macaluso |
| D345,081 S | 3/1994 | Adami et al. |
| 5,392,969 A | 2/1995 | Usery |
| 5,407,640 A | 4/1995 | Iles |
| 5,458,638 A | 10/1995 | Kuslich et al. |
| 5,518,909 A | 5/1996 | Banes |
| 5,554,536 A | 9/1996 | Rising |
| 5,593,891 A | 1/1997 | Banes |
| 5,604,130 A | 2/1997 | Warner |
| 5,652,142 A | 7/1997 | Barker et al. |
| 5,782,035 A * | 7/1998 | Locke et al. ............ 47/79 |
| 6,037,141 A | 3/2000 | Banes |
| 6,048,723 A | 4/2000 | Banes |
| 6,156,566 A | 12/2000 | Bryant |
| 6,218,178 B1 | 4/2001 | Banes |
| 6,790,655 B2 * | 9/2004 | Lyman et al. ............ 435/305.4 |

* cited by examiner

FLUID CONTAINMENT FOR LABORATORY CONTAINERS

This application claims the benefit of U.S. Provisional Application Ser. No. 60/458,925, filed on Mar. 31, 2003.

BACKGROUND OF THE INVENTION

1. Field of the Invention

The invention relates to culture plates or dishes with a guard for preventing inadvertent splashing of fluid from the culture plate or dish.

2. Description of the Related Art

Culture plates or dishes are used for culturing cells, bacteria or other biological materials. The typical culture dish is formed from a transparent plastic and has a substantially flat bottom wall, a short side wall enclosure that extends up from the bottom wall and an open top. The bottom wall typically is circular and the side wall typically is cylindrical. However, rectangular culture dishes are known.

A liquid growth media is placed in the culture dish and a small sample of the cells, bacteria or other biological materials are placed in the liquid growth material. A transparent cover then may be placed over the open top of the side wall to provide a substantially controlled environment in which growth will occur. Samples of the materials growing in the culture dish may be taken periodically to assess characteristics of the sample over time. Additionally, controlled amounts of liquid media may have to be added to or removed from the culture dish periodically.

The culture dish may have to be moved from one place in a laboratory to another. Such movement necessarily requires acceleration, deceleration and directional changes of the culture dish. These movements create a wave phenomena in the liquid media stored in the culture dish. As noted above, the side walls of a culture dish are very short, and hence even a small wave in the liquid media can cause the liquid media to splash out of the culture dish. Many culture dishes have a bottom wall with a fairly large surface area (e.g., 500 cm$^2$). The wave effects generated in such a large culture dish easily can exceed the height of the side wall, and hence significant amounts of liquid media can splash from the culture dish. Splashing reduces the volume of liquid media and biological materials in the culture dish, and hence can affect the laboratory analysis. Additionally, splashing of liquid media and other biological materials can cause contamination in the laboratory. For example, liquid media in one culture dish can inadvertently splash into an adjacent culture dish.

The problem of splashing from the culture dish has been known, and solutions to that problem have been considered. For example, U.S. Pat. No. 5,593,891 shows a culture dish with a circular bottom wall, a cylindrical side wall and a splash guard extending inwardly from the side wall. In some embodiments, the splash guard is formed unitarily with the side wall. However, these unitary structures are difficult to mold. In other embodiments, however, the splash guard is snapped into engagement with the mounting structure formed circumferentially on the side wall at or near the open top. In still other embodiments, the splash guard telescopes over or into the open top of the side wall. Splash guards that telescope over the side wall are undesirable because they add to the overall dimensions required for the culture dish.

Rectangular or square culture dishes have advantages over round culture dishes with cylindrical side walls. For example, round culture dishes can be arranged on a support surface with the cylindrical side wall of each culture dish being tangent to the cylindrical side walls on as many as four other identical culture dishes. This spacial arrangement of culture dishes result in substantial dead space between the points of tangency. Hence, circular culture dishes result in an inefficient use of space. Additionally, biological specimens are likely to grow differently at different locations in a culture dish based on environmental factors, such as the location and angle of light and minor temperature variations due to local environmental conditions. It is difficult to ensure uniform orientation of round culture dishes after the culture dishes have been moved for sampling or replenishment of the liquid growth media. Additionally, it is difficult to measure variations in the growth characteristics of cultures at various locations across the bottom wall of the culture dish. Still further, it is difficult to pour liquid media from a round culture dish in view of the relatively large radius of curvature on the cylindrical side wall.

Square and rectangular culture dishes overcome the above-identified problems. In particular, square culture dishes can be arranged close together, thereby achieving an efficient use of space in a laboratory. Square culture dishes also are easily oriented on the supporting surface, and rectangular quadrants can be assigned easily to a square culture dish to determine and track differences in culture growth characteristics at different coordinates across the bottom wall. However, square culture dishes are not conducive to receiving a separately mountable splash guard. More particularly, a splash guard on a circular culture dish will exert forces uniformly against the cylindrical side wall of the dish. In theory, the side walls of a square culture dish could be formed with a bead or groove for engaging a mating structure on a square splash guard. However, it is difficult to achieve uniform forces along such a rectilinear array of interengaged surfaces, and stress concentrations are likely to exist. The existence of non-uniform engagement forces around the peripheries of a square splash guard can complicate the mounting of the splash guard and can damage either the splash guard or the side walls. Additionally, gaps may exist between mating surfaces of the square splash guard and the side wall. The liquid media can splash through or can accumulate in such gaps. Liquid media that accumulates in gaps between the square splash guard and the side walls may cause a culture growth that is much different than the culture growth on the bottom wall of the dish. Thus, although square culture dishes offer advantages over cylindrical culture dishes, the square culture dishes are not well suited to the splash guards that have been employed with round culture dishes.

SUMMARY OF THE INVENTION

The invention is a culture dish assembly. The assembly includes a substantially square culture dish unitarily formed from a rigid transparent plastic material. The culture dish includes a bottom wall, a side wall enclosure extending unitarily from the bottom wall and an open top. The bottom wall is substantially planar and substantially square, but may include rounded corners. The dimensions of the bottom wall may vary from one laboratory application to another. For example, the bottom wall may have an area of approximately 500 cm$^2$. A plurality of short support walls may extend down from the lower surface of the bottom wall to support the bottom wall in spaced relationship to a supporting surface and to permit efficient stacking of culture dish assemblies.

The side wall enclosure includes two opposed pairs of substantially planar side panels that extend up from the respective edges of the square bottom wall. The planar panels of the side wall enclosure are joined consecutively to one another by rounded corners. One corner, however, may be truncated to provide a frame of reference for orienting the culture dish. The planar panels of the side wall enclosure may taper outwardly at further distances from the bottom wall to facilitate molding. The side wall enclosure includes a continuous peripheral top edge aligned substantially parallel to the bottom wall of the culture dish. The planar panels may be provided with indicia to show fluid volumes corresponding to different fluid levels in the culture dish.

The inner surface of each planar side panel preferably has a plurality of splash guard mounts. The splash guard mounts preferably are at locations near the top edge of the side wall enclosure. Each splash guard mount preferably is elongated and has a direction of elongation substantially parallel to the bottom wall and parallel to the top edge. The splash guard mounts are disposed entirely on the planar panels of the side wall enclosure and are spaced from the corners. The total length of the splash guard mounts on each planar panel is preferably substantially less than half the length of the respective panel. The splash guard mounts preferably are projections, but at least some splash guard mounts may be recesses.

The culture dish assembly further includes a splash guard. The splash guard includes a generally planar rectangular frame-shaped top wall with outer and inner peripheries. The outer periphery has two opposed pairs of straight side edges connected by rounded outer corners. Additionally, the outer periphery may substantially match the outer periphery defined by the top edge of the side wall enclosure. The inner periphery has two pairs of opposed edges connected by rounded inner corners. An inner peripheral rim may project down a short distance from the inner periphery of the splash guard and preferably is continuous about the inner periphery of the top wall.

The splash guard may further include two opposed pairs of peripheral engagement flanges that extend down a short distance from the top wall of the splash guard at locations spaced inwardly from the respective straight side edges of the outer periphery. The engagement flanges are disposed to engage inner peripheral surface areas of the planar panels on the side wall enclosure of the culture dish. The engagement flanges of the splash guard may further include spaced apart elongate wall mounts that are disposed to snap into engagement with the respective splash guard mounts on the inner surfaces of the planar panels when the top wall of the splash guard seats on the top edge of the side wall enclosure. The engagement of the wall mounts with the splash guard mounts provides sufficient interference to provide an audible and tactile indication of proper seating of the splash guard on the side wall enclosure and to prevent inadvertent separation of the splash guard from the side wall enclosure.

The splash guard may include a small concave cut-out at one corner of the outer periphery of the top wall. The cut out is provided for those situations where it may be desired to pour liquid media from the culture dish.

The culture dish assembly may further include a cover. The cover preferably is formed unitarily from a rigid transparent plastic material and includes a substantially planar square top wall with an outer periphery defined by two opposed pairs of straight sides. The straight sides are joined by rounded corners. The shape of the top wall of the cover may conform to the outer periphery of the top wall of the splash guard. The top wall may include alpha-numeric indicia at spaced locations along two adjacent edges for identifying grids in the culture dish assembly. Thus, quantitative and qualitative assessments of culture growth can be made based on locations in the culture dish.

The cover further includes a peripheral skirt that extends down from the outer periphery of the top wall. The skirt may be flared outwardly at further locations from the top wall to facilitate molding and to facilitate nesting of the cover over the subassembly of the culture dish and splash guard. The length of the peripheral skirt from the top wall is less than the length of the side wall enclosure from the bottom wall of the culture dish. Thus, the bottom of the skirt will not impede complete seating of the cover on the culture dish when the culture dish is supported on a planar surface.

The culture dish assembly may be used by initially mounting the splash guard to the open top of the culture dish. The mounting of the splash guard preferably is accompanied by both a tactile and audible indication of proper position as the wall mounts of the engagement flanges of the splash guard engage the splash guard mounts on the inner surfaces of the planar panels of the culture dish. The engagement flanges do not extend continuously through the rounded corners of the side wall enclosure of the culture dish. Thus, there are no problems of achieving proper mounting stresses through the corners. However, planar regions of the top wall of the splash guard outwardly from the engagement flanges will be seated in substantially face-to-face engagement with the entire top edge of the side wall enclosure of the culture dish. The only area where the splash guard may be separated from the top edge of the side wall enclosure may exist in one corner of the splash guard on those embodiments where a concave pouring cut-out is provided. The wave mechanics, however, are such that splashing at such a corner pouring cut-out is unlikely. The culture dish assembly is employed by placing a selected amount of a liquid growth media in the culture dish and then depositing an appropriate biological material that is to be grown or otherwise developed under laboratory conditions. The cover then may be telescoped over the subassembly of the culture dish and splash guard. The cover may be removed periodically for replenishing the liquid media or for scraping or otherwise retrieving samples of the culture. The cover may be replaced after achieving such access to the liquid in the culture dish. The culture media may be poured from the subassembly of the culture dish and the splash guard by tilting the subassembly toward a corner on those embodiments where the top wall of the splash guard is provided with a concave pouring cut-out.

The splash guard may require periodic separation from the culture dish for a more thorough access to culture growth in the dish. As noted above, the wall mounts of the engagement flanges of the splash guard engage the splash guard mounts on the inner surfaces of the planar panels of the culture dish. This engagement is sufficient to hold the splash guard in position and to provide a tactile and audible indication of proper positioning. This engagement also can slightly complicate removal of the splash guard from the culture dish. Removal of the splash guard from the culture dish can be facilitated by providing at least one lift element on the splash guard to facilitate separation of the splash guard from the culture dish. For example, the outer periphery of the frame-shaped top wall may be formed with at least one tab projecting outwardly a sufficient distance to project beyond the side wall enclosure of the culture dish. The tab can be engaged digitally to facilitate separation of the splash guard from the culture dish. A plurality of such removal tabs may be provided, and most preferably a tab is provided on each of the straight side edges on the outer periphery of the planar rectangular frame-shaped top wall of the splash guard.

The splash guard can include other structures for facilitating removal from the culture dish. For example, at least one cut-out may be formed on the inner periphery of the frame-shaped top wall of the splash guard. The cut-out may be configured for engagement by a finger or a laboratory tool. A plurality of such cut-outs may be provided. For example, a cut-out may be provided on each of the edges that extend between the rounded corners defined by the inner periphery of the frame-shaped top wall of the splash guard.

In still a further alternate, a pull handle may be formed on the upper surface of the frame-shaped top wall of the splash guard. The pull handle can be connected to the frame-shaped top wall by a living hinge so that the pull handle can be rotated between a substantially upright position and a substantially low profile condition substantially adjacent the top surface of the frame-shaped top wall. The handle can be rotated in to the upright position to facilitate engagement between a thumb and forefinger or by a laboratory tool so that the splash guard can be lifted easily from the culture dish. Alternatively, the handle can be rotated about the living hinge and into substantially face-to-face engagement with the frame-shaped top wall to provide a relatively low profile. The provision of the handle and/or the provision of cut-outs or finger slots on the inner periphery of the top wall instead of the above-described pull handle permits a splash guard that can nest slightly into the open top defined by the side wall enclosure of the culture dish. The amount of nesting of the splash guard into the open top defined by the side wall enclosure can be limited due to the slight outward flaring of the side wall enclosure that is provided to facilitate molding of the culture dish. This option enables the assembly of the culture dish and splash guard to have a low profile that does not exceed the overall height of the culture dish. Additionally, this nesting of the splash guard partly into the open top of the side wall enclosure can provide an alternate arrangement for sealing the splash guard to the side wall enclosure. For example, the splash guard can be formed with a gasket that extends around the outer periphery of the frame-shaped top wall of the splash guard to provide a hermetic seal between the side wall enclosure of the culture dish and the splash guard.

The above-described cover can completely seal the open top defined by the inner periphery of the splash guard. However, complete sealing is not always desired. Rather, the culture medium in the culture dish may require a breathable closure that permits gas exchange. For these situations, the frame-shaped top wall of the culture dish may be formed with a plurality of breathing lugs extending up from the top surface of the top wall for permitting the top wall of the cover to be supported in spaced relationship to locations on the top wall of the splash guard between the breathing lugs.

BRIEF DESCRIPTIONS OF THE DRAWINGS

DETAILED DESCRIPTION

Figure 1:
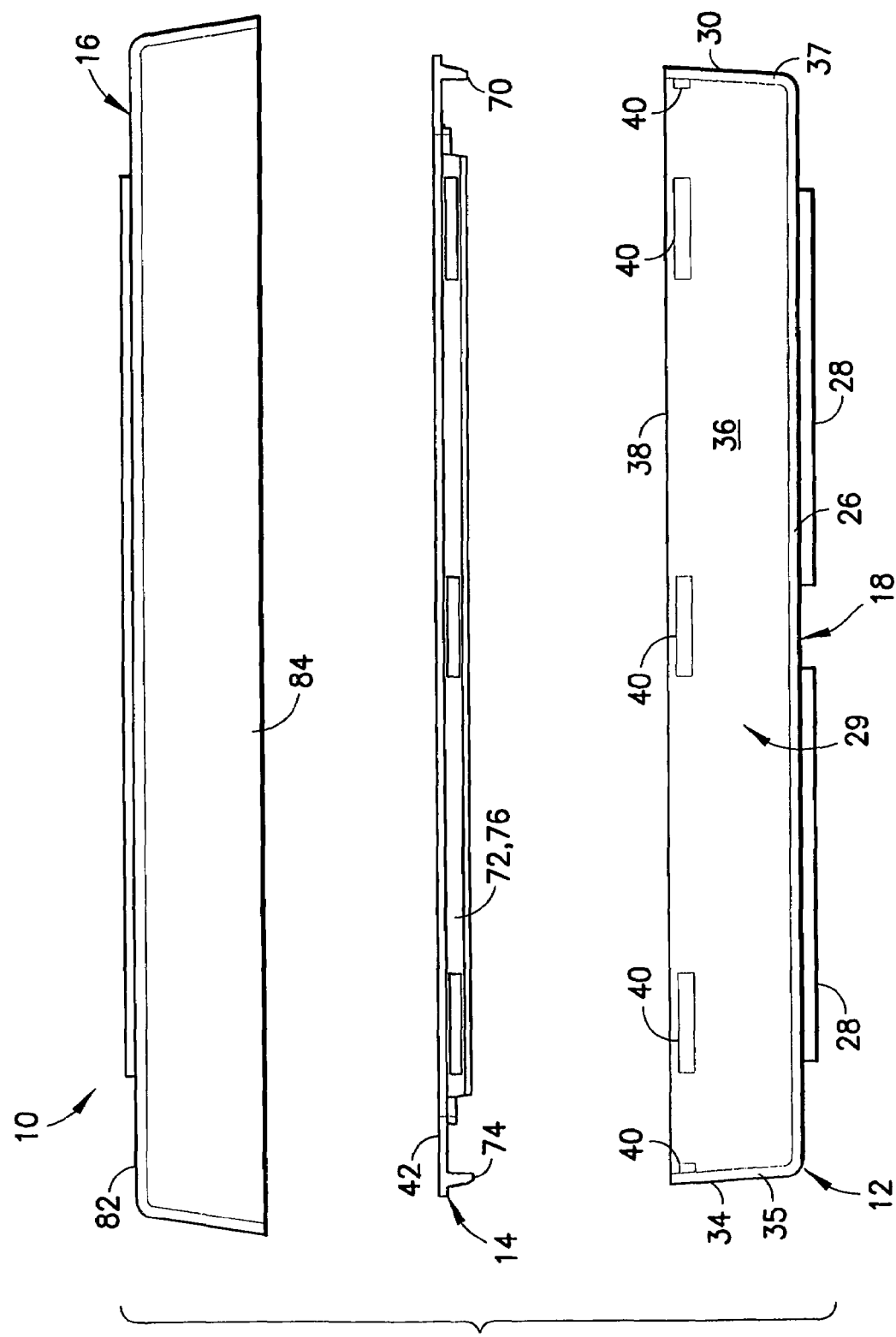
FIG. 1 is an exploded side elevational view of a culture dish assembly in accordance with the invention.
Figure 6:
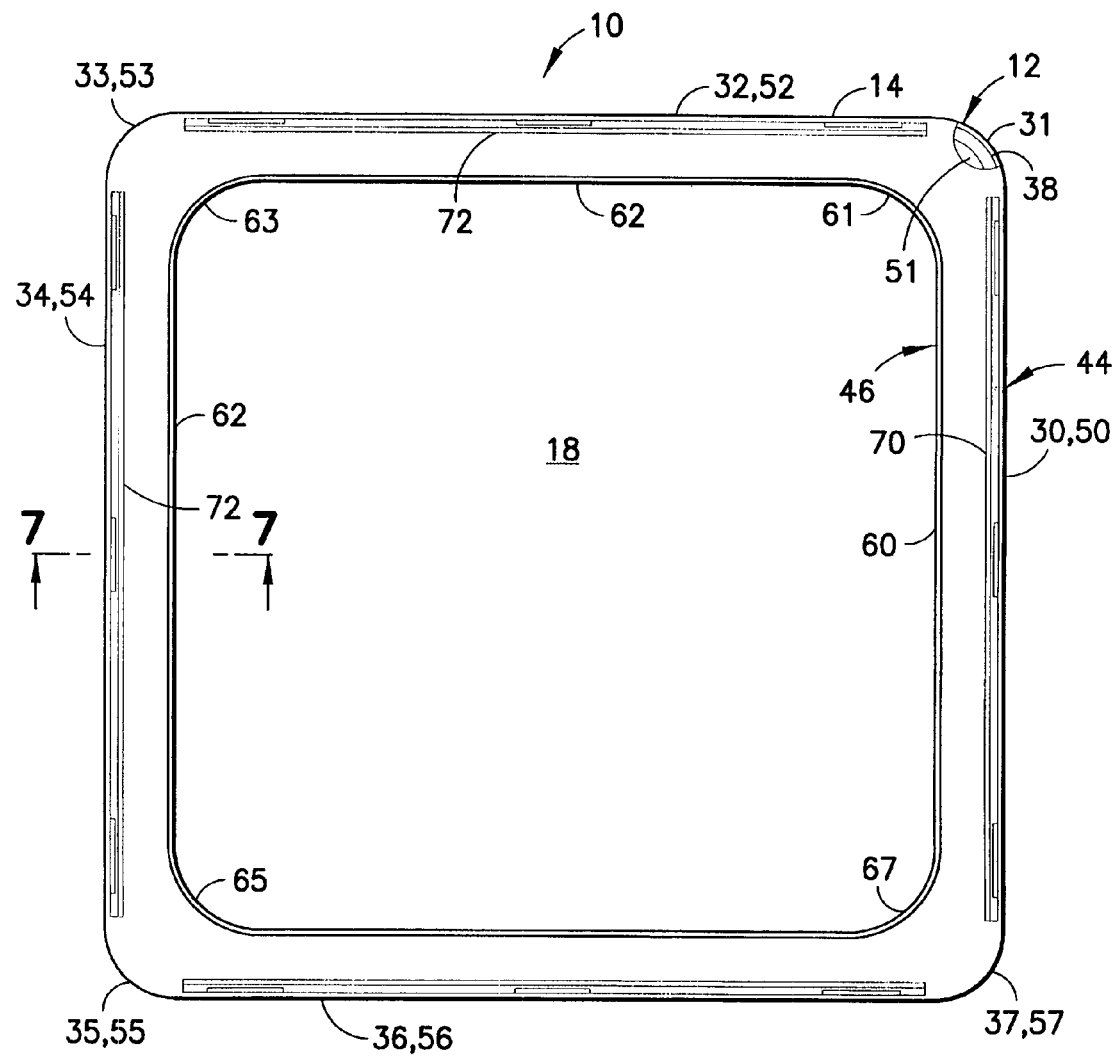
FIG. 6 is a top plan view of the culture dish assembly in its fully assembled condition.
Figure 7:
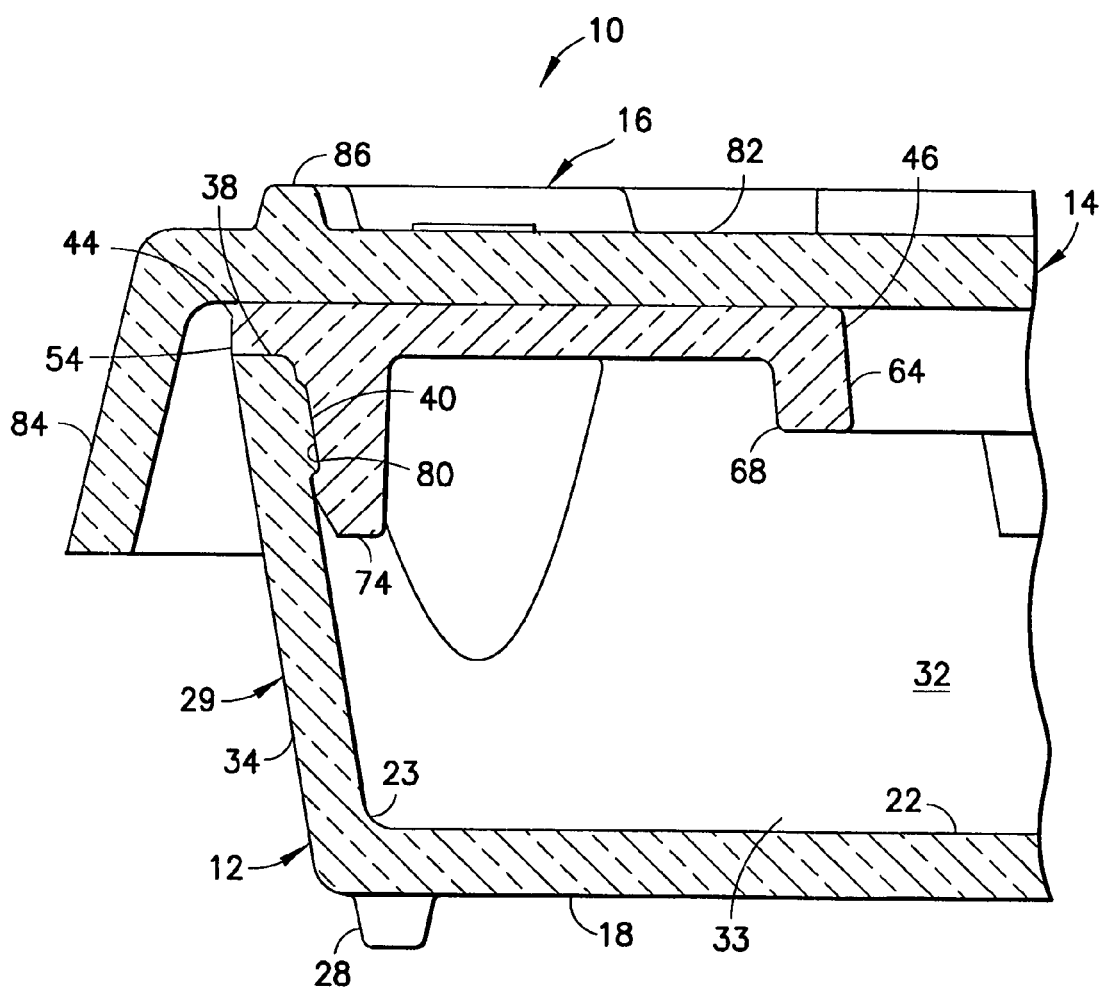
FIG. 7 is a cross-sectional view taken along line 7-7 in FIG. 6.

A culture dish assembly in accordance with the invention is identified generally by the numeral 10 in FIGS. 1, 6 and 7. Culture dish assembly 10 includes a culture dish 12, a splash guard 14 and a cover 16.

Figure 2:
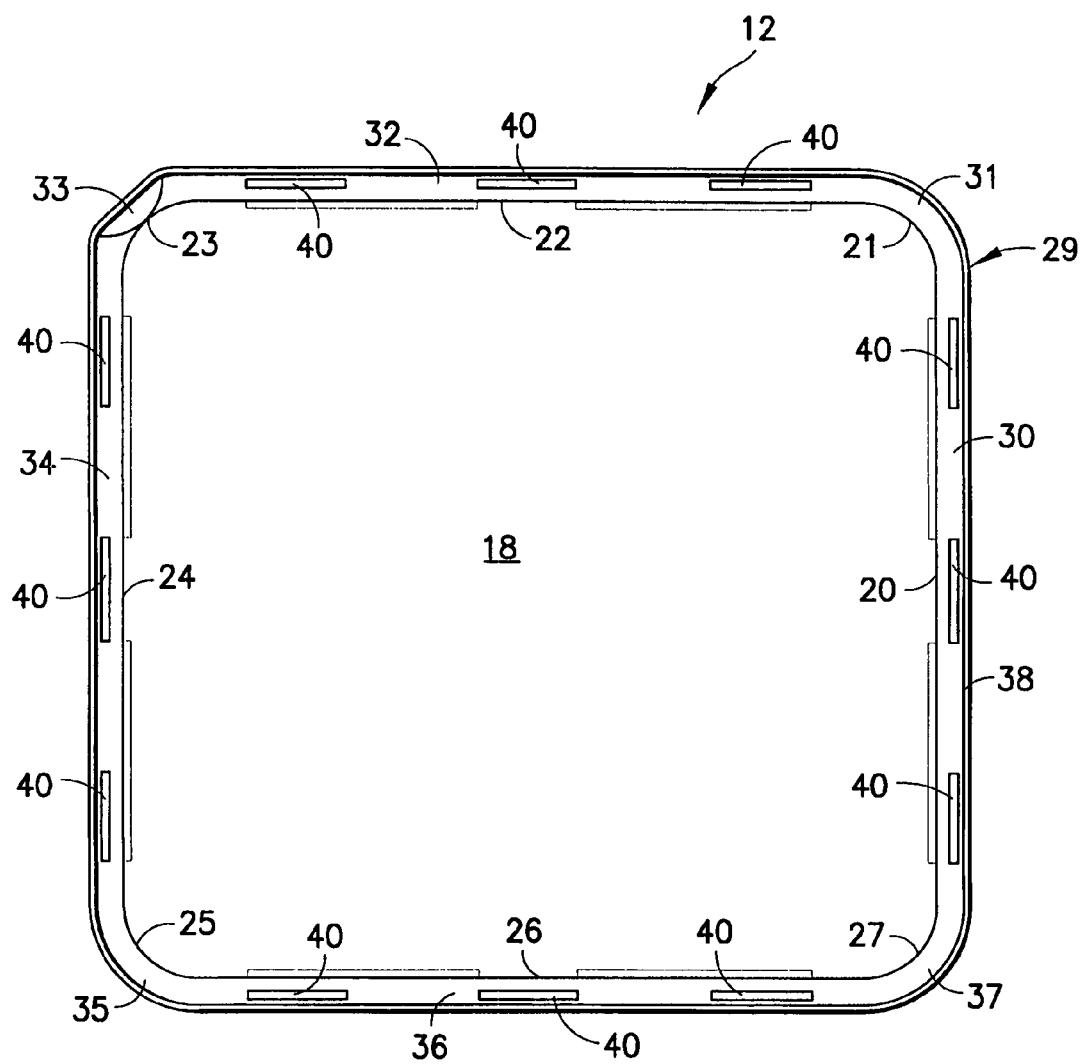
FIG. 2 is a top plan view of the culture dish.

Culture dish 12 is unitarily molded from a transparent rigid plastic material and includes a substantially planar bottom wall 18. Bottom wall 18 is substantially square, and hence has four substantially equal sides 20, 22, 24 and 26. Sides 20 and 24 are opposed and substantially parallel, while sides 22 and 26 are opposed and substantially parallel. Rounded corners 21, 23, 25 and 27 extend continuously between the adjacent sides 20, 22, 24 and 26 as shown in FIG. 2. A plurality of bottom supports 28 extend down from peripheral regions of bottom wall 18. Supports 28 are substantially identical to one another and permit bottom wall 18 to be supported in slightly spaced relationship to a planar supporting surface such that bottom wall 18 is parallel to the planar supporting surface. Supports 28 also contribute to efficient stacking of culture dish assemblies as explained below.

Culture dish 12 further includes a side wall enclosure 29. Side wall enclosure 29 includes four planar side panels 30, 32, 34 and 36 extending up respectively from the sides 20, 22, 24 and 26 of bottom panel 18. The side wall enclosure 29 further includes corners 31, 33, 35 and 37 extending up respectively from the corners 21, 23, 25 and 27 of the bottom wall 18. Corners 31, 33, 35 and 37 extend continuously between the adjacent side wall panels 20, 22, 24 and 26 as shown in FIG. 2. Corners 31, 35 and 37 are rounded. However, corner 33 is truncated to facilitate orientation and to provide a frame of reference for culture dish 12. Side wall enclosure 29 further includes a continuous peripheral top edge 38 which defines the portion of side wall enclosure 29 furthest from bottom wall 18. Top edge 38 is substantially planar about the periphery of culture dish 12 and substantially parallel to bottom wall 18. Side wall enclosure 29 flares outwardly and uniformly between bottom wall 18 and top edge 38 to facilitate molding. Portions of culture dish 12 bounded by top edge 38 define a widely open top to culture dish 12.

Side wall enclosure 29 further includes a plurality of elongate projections 40 on inwardly facing surfaces of each side wall panel 30, 32, 34 and 36. Each projection 40 is spaced slightly from top edge 38. Additionally, projections 40 each define a substantially elongate rectangle with a longitudinal direction extending substantially parallel to top edge 38. Projections 40 all are spaced from corners 31, 33, 35 and 37 respectively of side wall enclosure 29. Projections 40 each define a length of approximately 2 cm and are spaced from one another by distances of approximately 6 cm. These relative distances may vary from one application to the next depending upon the dimensions of the bottom wall 18. However, in preferred embodiments, the spacing between projections 40 exceeds the length of each projection 40 and preferably the spacing between projections 40 is about three times the length of each projection 40.

Figure 3:
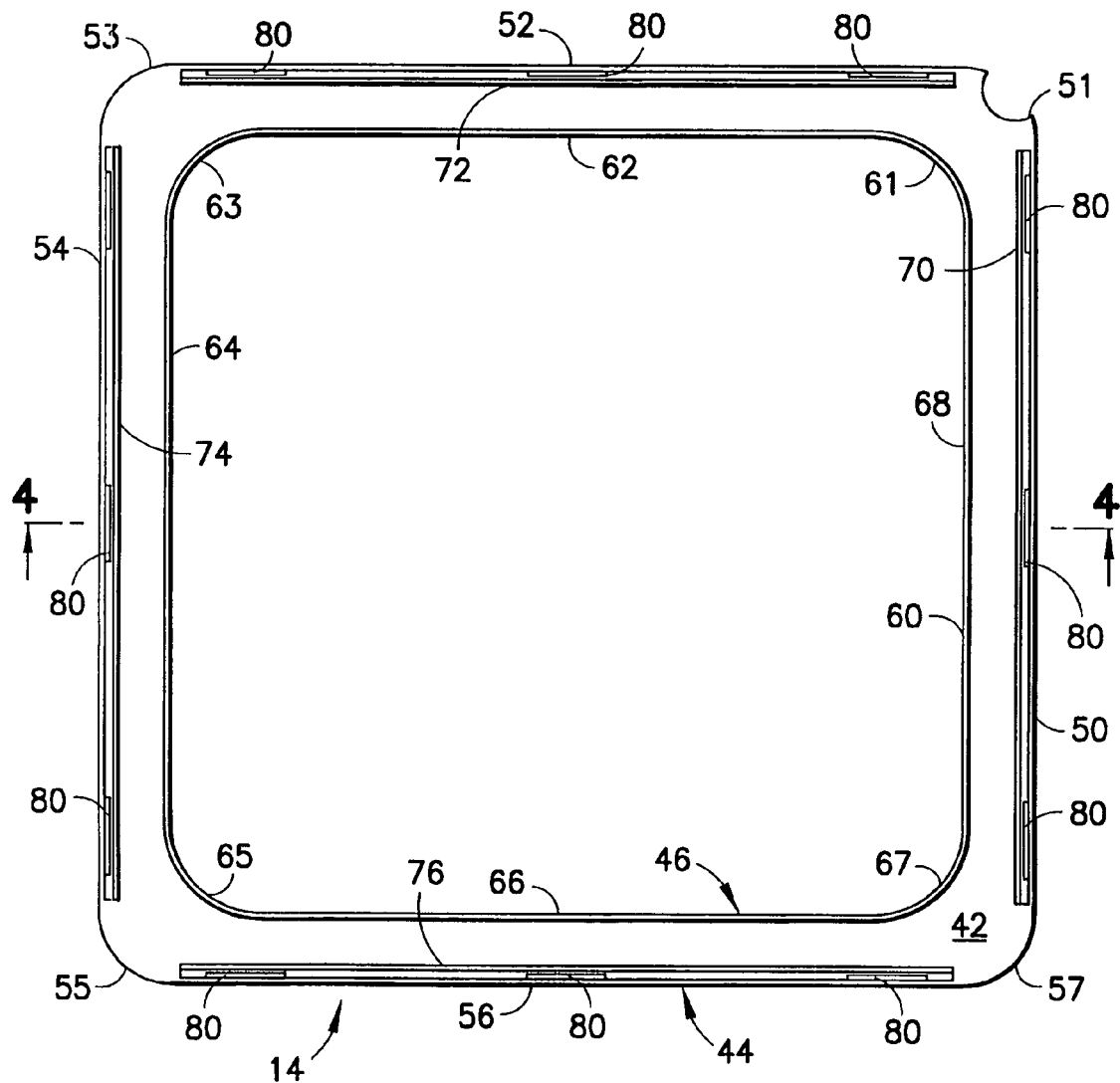
FIG. 3 is a top plan view of the splash guard.

Splash guard 14 includes a generally planar frame-shaped top wall 42 with an outer periphery 44 and an inner periphery 46. The outer periphery 44 is dimensioned to substantially register with outer peripheral portions of top edge 38 of side wall enclosure 28 on culture dish 12. Outer periphery 44 includes straight side edges 50, 52, 54 and 56 and arcuate corners 51, 53, 55 and 57 as shown in FIG. 3. Corners 53, 55 and 57 are convexly arcuate. However, corner 57 is concavely arcuate to define a pouring opening to facilitate pouring of media from culture dish assembly 10. Concave corner 51 is not required and will not be provided on many embodiments.

Inner periphery 46 include straight edges 60, 62, 64 and 66 and corners 61, 63, 65 and 67 extending continuously between the straight edges as shown in FIG. 3. Straight edges 60, 62, 64 and 66 are spaced from the corresponding straight edges 50, 52, 54 and 56 of outer periphery 44 by about 1.5 cm. However, concave rounded corners 61, 63, 65 and 67 define larger radii than the corresponding outer corners 51, 53, 55 and 57. Hence, radial dimensions of top wall 42 at the corners exceeds the distance between outer and inner peripheries 44 and 46 at locations spaced from the corners.

Figure 4:
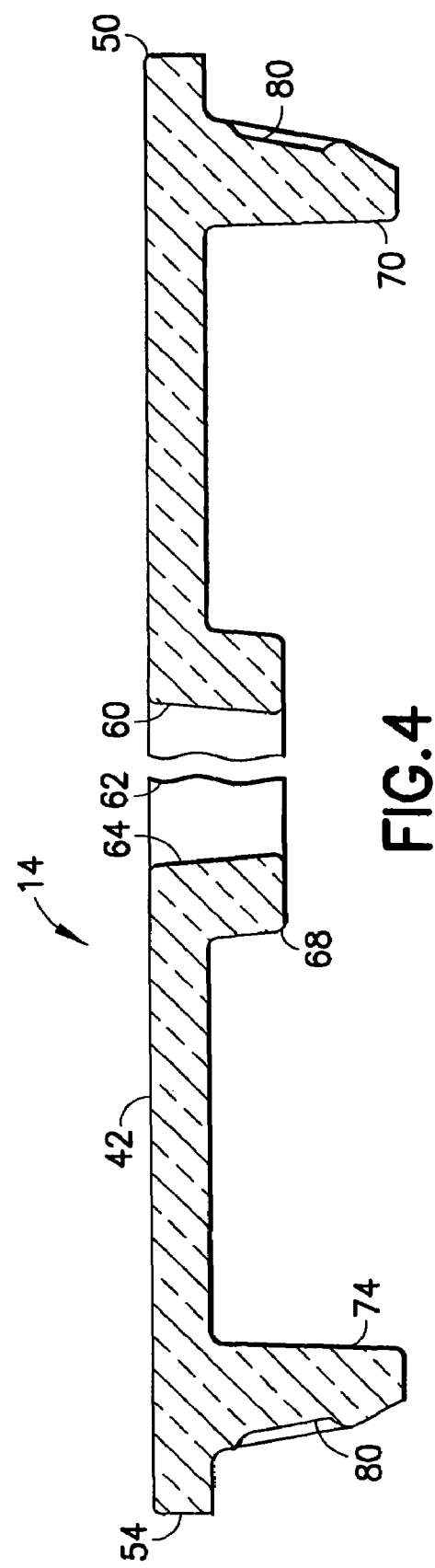
FIG. 4 is a cross-sectional view taken along line 4-4 in FIG. 3.
Figure 5:
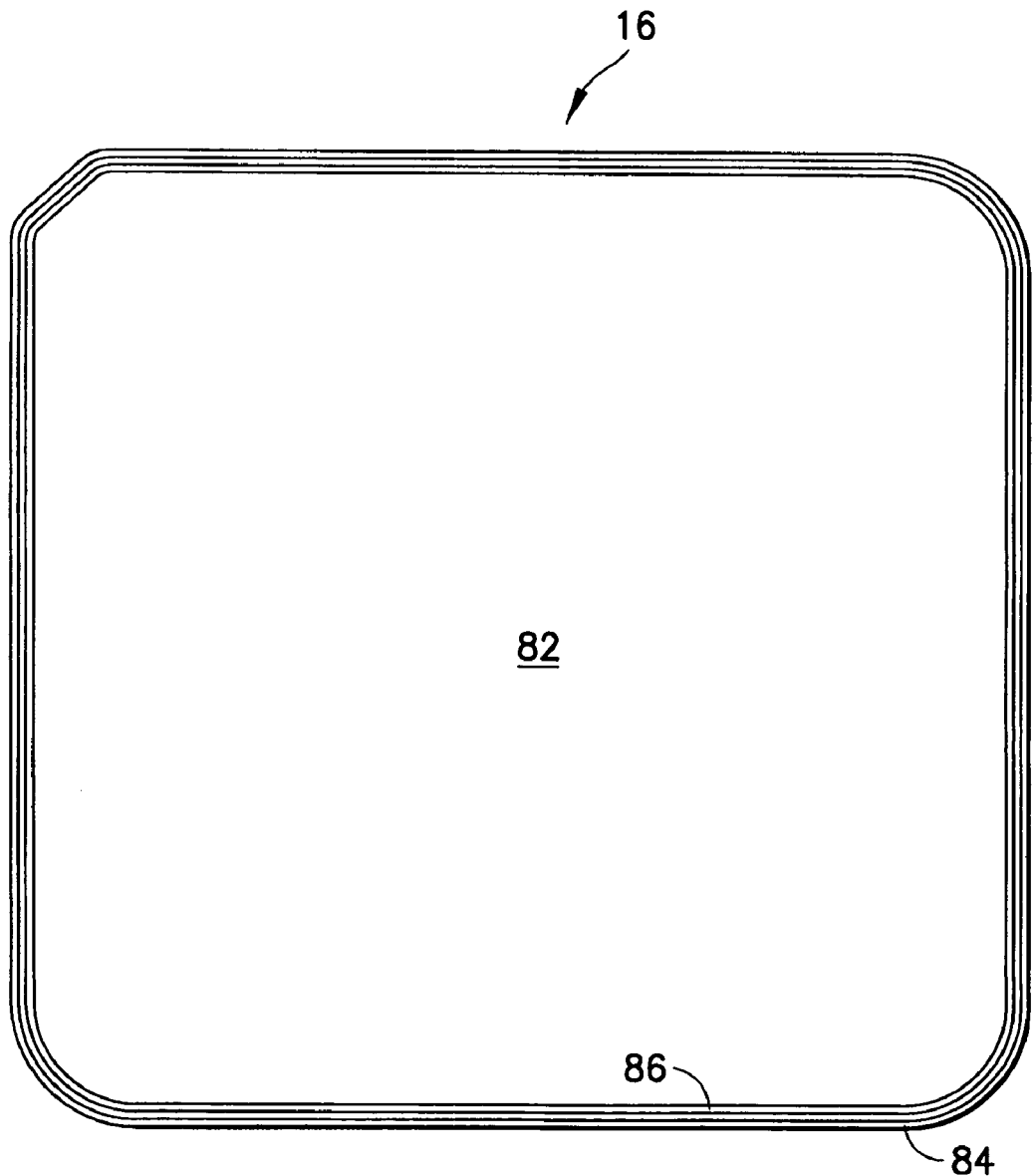
FIG. 5 is a top plan view of the cover.

Splash guard 14 further includes an inner peripheral lip 68 that extends down from top wall 42 continuously around inner periphery 46, as shown in FIG. 4. Peripheral lip 68 helps contain any liquid media that may splash from side wall enclosure 29.

Splash guard 14 further includes substantially planar engagement flanges 70, 72, 74 and 76 that extend down from top wall 42 at locations spaced inwardly from straight edges 50, 52, 54 and 56 respectively of outer periphery 44. Engagement flanges 70, 72, 74 and 76 are disposed respectively to telescope into nested engagement with inner surface regions of planar side wall panels 30, 32, 34 and 36 respectively of side wall enclosure 29. Each engagement flanges extends from top wall 42 a distance of about 0.5 cm. Significantly, each engagement flanges 70, 72, 74 and 76 are disposed to terminate at locations spaced from corners 31, 33, 35 and 37 of side wall enclosure 29 on culture dish 12. Outwardly facing surfaces of engagement flange are tapered inwardly, as shown in FIG. 4 to facilitate molding and to facilitate nesting with side wall enclosure 29 of culture dish 12. Additionally, outwardly facing surfaces of each engagement flange 70, 72, 74 and 76 are formed with a plurality of elongate spaced apart engagement recesses 80. Engagement recesses 80 are dimensioned and disposed to snap into engagement with projections 40 on planar panels 30, 32, 34 and 36 of side wall enclosure 29.

Cover 16 includes a square substantially planar top wall 82 and a downwardly depending skirt 84. Skirt 84 flares slightly outwardly to facilitate molding. Additionally, skirt 84 is configured to telescope over and nest on either top edge 38 of culture dish 12 or on splash guard 14. The extension of skirt 84 from top wall 82 of cover 16 is shorter than the height of side wall enclosure 29. Hence, skirt 84 will not impede complete seating of cover 16 on culture dish 12. Peripheral regions of top wall 82 of cover 16 preferably are provided with graduated indicia along at least two edges to identify grids for quantitatively and/or qualitatively identifying different characteristics of culture growth in culture dish 12.

Culture dish assembly 10 is used by removing cover 16 and depositing a selected volume of liquid growth media in culture dish 12 along with an appropriate biological sample. Cover 16 then is replaced. A plurality of such culture dishes may be prepared in this manner and may be arranged in side-to-side relationship with one another on a supporting surface. Additionally, a plurality of culture dish assemblies 10 may be stacked by placing lower supports 28 of one culture dish assembly 10 within the area bounded by peripheral rib 86 projecting from top wall 82 of cover 16 of another culture dish assembly 10.

Culture dish assembly 10 may have to be moved from time-to-time for replenishing the liquid growth media or for extracting samples for analysis. The acceleration and deceleration that necessarily is associated with movement of culture dish assembly 10 affects the liquid media and generates a wave action therein. Such wave action has the potential of permitting liquid media and biological samples growing the culture dish to splash from the culture dish. However, splash guard 14 is snapped securely into engagement with side wall enclosure 29 of culture dish 12. This engagement ensures that portions of top wall 42 of splash guard 14 adjacent outer periphery 44 seat securely on top edge 38 of side wall enclosure 29. Projections 40 on side wall panels 30, 32, 34 and 36 of culture dish 12 engage in the correspondingly positioned and dimensioned recesses in engagement panels 70, 72, 74 and 76 of splash guard 14 without any lateral engagement through corners 31, 33, 35 and 37 of culture dish 12. Hence, there are no stress concentrations that could damage culture dish 12 or splash guard 14 or that could urge top wall 42 of splash guard 14 into a non-planar condition that would permit escape of any splashed liquid between splash guard 14 and top edge 38 of side wall enclosure 29. Additionally, interengaged areas of projections 40 and recesses 68 make up a minor part of the inner peripheral surfaces of side wall enclosure 28. Accordingly, there are few areas for liquid media to accumulate and grow in a manner that might be inconsistent with the growth occurring on or near bottom wall 18 of culture dish 12.

Downwardly projecting inner peripheral lip 68 that extends around inner periphery 46 of splash guard 14 further prevents splashed liquid from exiting through the area bounded by inner periphery 46. More particularly, liquid redirected by inner peripheral surfaces of side wall enclosure 29 will be directed upwardly and inwardly. Inner peripheral lip 68 will redirect a major portion of any such splashed liquid down toward bottom wall 18.

The mechanics of the wave action of liquid in culture dish 12 are such that a major portion of liquid urged against inner surface regions of side wall enclosure 29 will be redirected off one of planar side panels 20, 22, 24 and 26. A much smaller percentage of waves in the liquid media will be moved directly into corners 21, 23, 25 and 27. Additionally, inner peripheral surfaces of side wall enclosure 29 will urge the liquid inwardly and upwardly as opposed to an upward and outward movement of liquid. Accordingly, there may be some instances where corner regions will not perform a critical splash-preventing function. Additionally, there may be instances where it will periodically be necessary to remove excess liquid media. Pouring provides a convenient way of removing excess liquid media. However, the separation of splash guard 14 to permit pouring could create the splashing that splash guard 14 is intended to avoid. Accordingly, there are some instances where splash guard 14 can have a concave corner 51. Concave corner 51 is spaced from convex corner 31 of side wall enclosure 29. Thus, excess liquid media can be poured from culture dish 12 without removing splash guard 14 and without creating a substantial likelihood of splashing liquid media.

Figure 8:
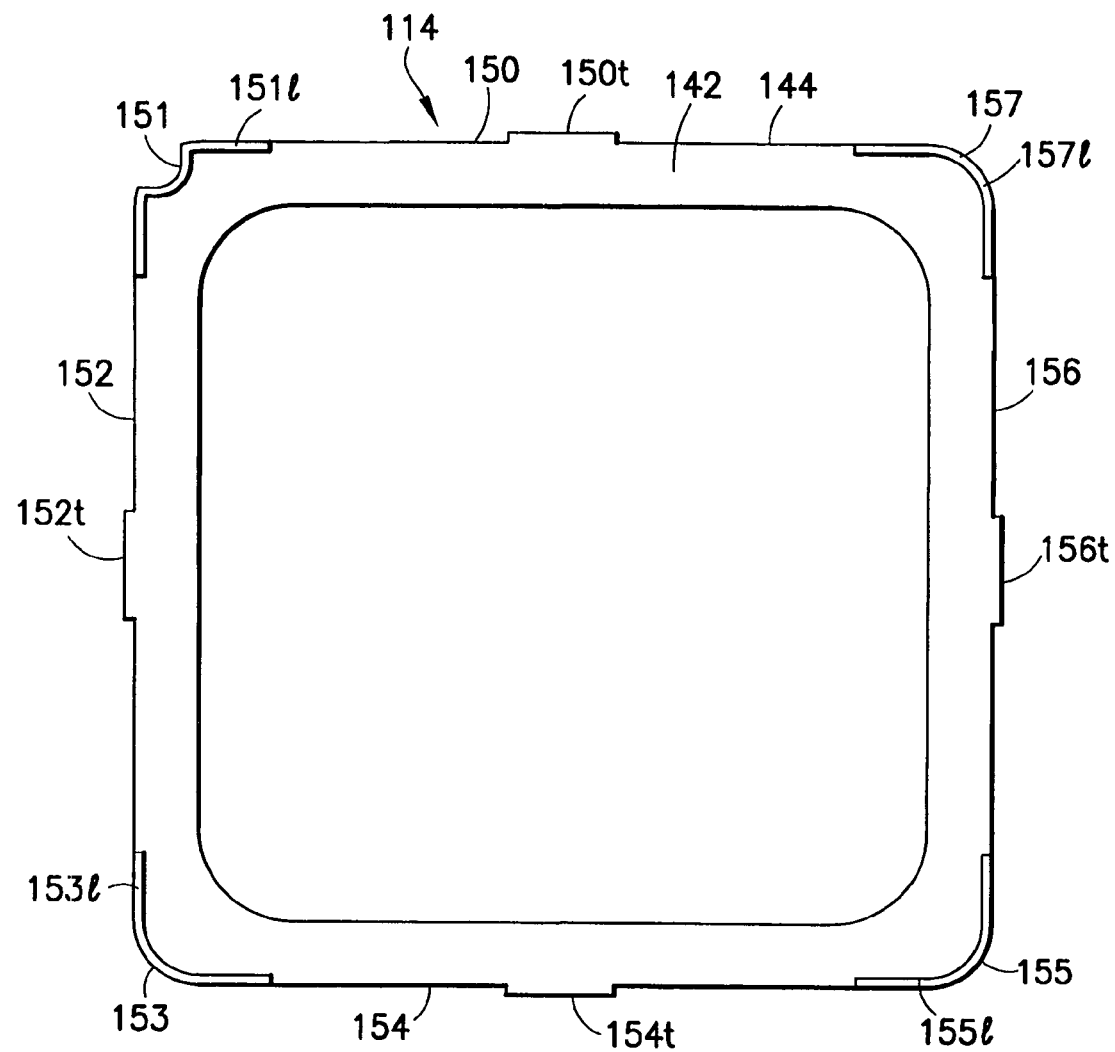
FIG. 8 is a top plan view of an alternate splash guard.
Figure 9:
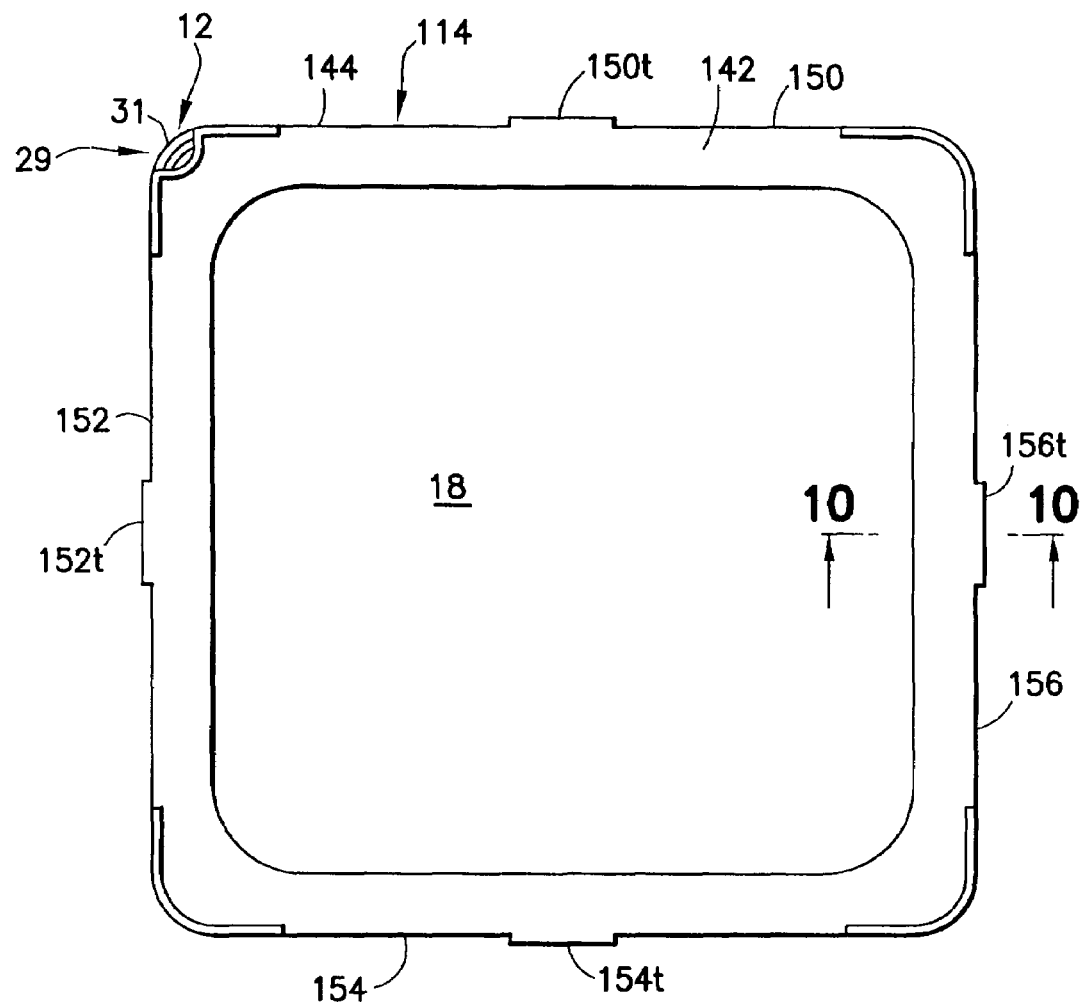
FIG. 9 is a top plan view of the splash guard of FIG. 8 mounted on the culture dish.
Figure 10:
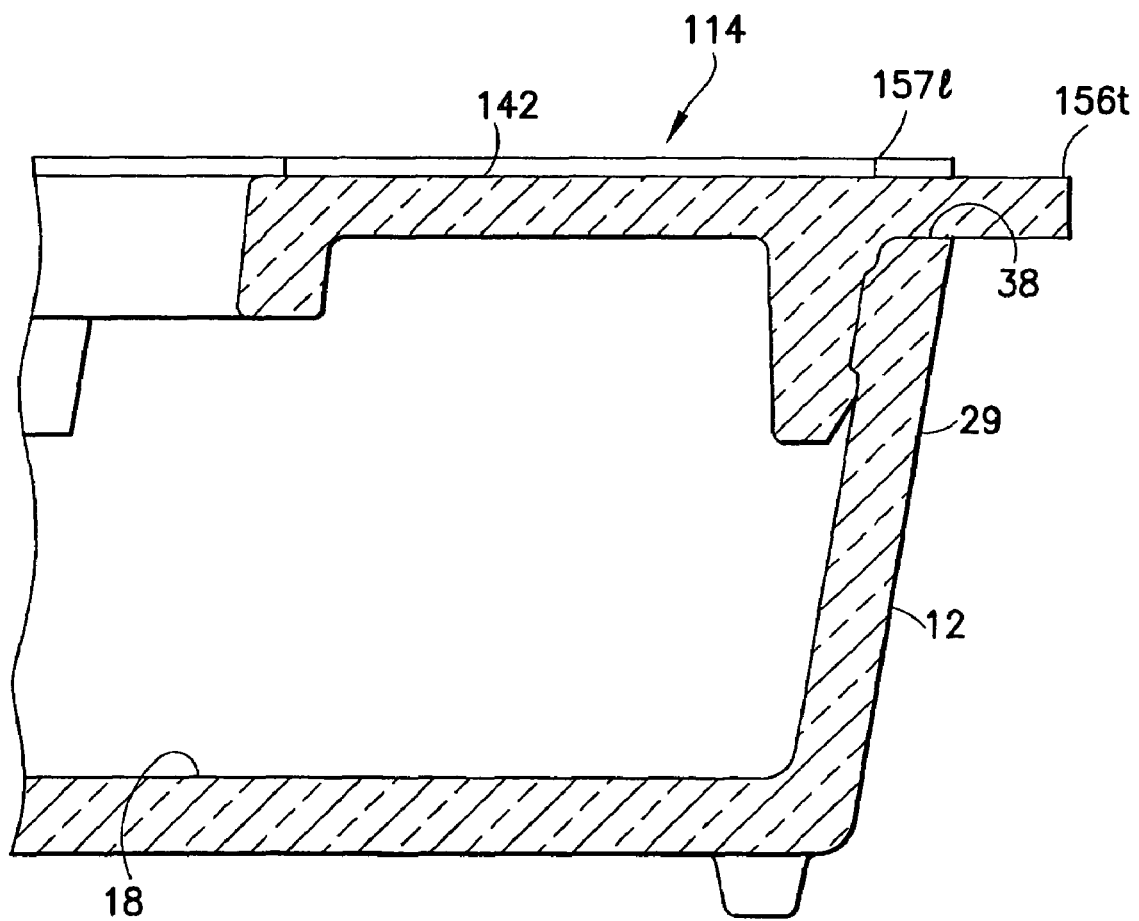
FIG. 10 is a cross-sectional view taken along line 10-10 in FIG. 9.
Figure 11:
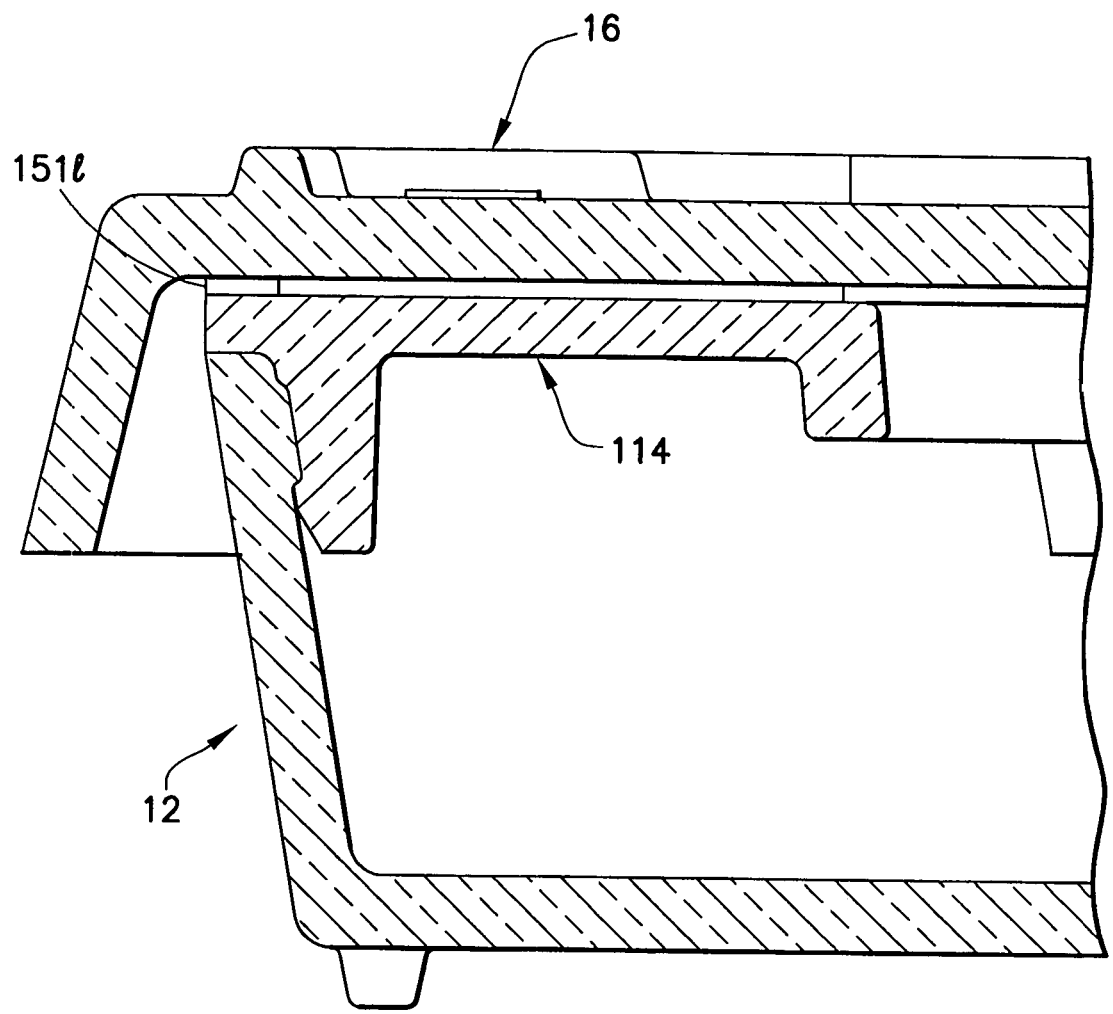
FIG. 11 is a cross-sectional view similar to FIG. 7, but showing the cover mounted on the second embodiment of the splash guard.

A second embodiment of a splash guard in accordance with the subject invention is identified generally by the numeral 114 in FIG. 8. Splash guard 114 is very similar to splash guard 14 described above and illustrated most clearly in FIGS. 3 and 4. Elements of splash guard 114 that are identical to splash guard 14 merely are identified by the same reference numerals herein, and a repeated description is not provided. Splash guard 114 differs from splash guard 14 in two significant respects. In particular, splash guard 114 includes a top wall 142 with an outer periphery 144. Outer periphery 144 has substantially straight outer side edges 150, 152, 154 and 156 and arcuate corners 151, 153, 155 and 157 as shown in FIG. 8. Substantially straight edges 150, 152, 154, and 156 are dimensioned and configured to substantially register with the outer periphery of top edge 38 of side wall enclosure 29 on culture dish 12. However, substantially straight edges 150, 152, 154 and 156 are characterized further by lift tabs 153t, 152t, 154t and 156t that extend outwardly beyond the outer periphery of side wall enclosure 29 when top wall 142 of splash guard 114 is seated on top edge 38 of side wall enclosure 29. Lift tabs 150t, 152t, 154t and 156t enable splash guard 114 to be lifted easily from culture dish 12 by a finger or by laboratory equipment. Removal of splash guard 114 can facilitate access to bottom wall 18 of the culture dish so that cells grown on bottom wall 18 can be scraped from culture dish 12 for laboratory analysis.

Splash guard 114 also differs from splash guard 14 in that top wall 142 includes upwardly projecting breathing lugs 151l, 153l, 155l and 157l in proximity to corners 151, 153, 155 and 157 respectively. Significantly, lugs 151l, 153l, 155l and 157l do not connect to one another. Hence, lugs 151l, 153l, 155l and 157l ensure that breathing spaces exist between lugs 151l, 153l, 155l and 157l to permit gas exchange between the interior of culture dish 12 and ambient surroundings when cover 16 is in place.

FIGS. 12-15 show a culture dish assembly 210 in accordance with a third embodiment of the subject invention. The culture dish assembly 210 includes a rectangular culture dish 212 that is very similar to culture dish 12 described and illustrated above. More particularly, culture dish 212 includes a bottom wall 218 and a side wall enclosure 229. However, side wall enclosure 229 of culture dish 212 does not include elongate projections comparable to elongate projections 40 on culture dish 12. Rather, interior surfaces of side wall enclosure 229 may be substantially smooth between top edge 238 of side wall enclosure 229 and bottom wall 218. Importantly, however, side wall enclosure 229 flares outwardly from bottom wall 218 to facilitate molding.

Culture dish assembly 210 further includes a splash guard 214 with a frame-shaped wall 242. Frame-shaped wall 242 includes an outer periphery 244 dimensioned to nest partly within side wall enclosure 229 of culture dish 212. Thus, outer periphery 244 of frame-shaped wall 242 of splash guard 214 is smaller than the inner periphery of side wall enclosure 229 adjacent top edge 238, but is larger than the inner periphery of side wall enclosure 229 adjacent bottom wall 218.

Figure 12:
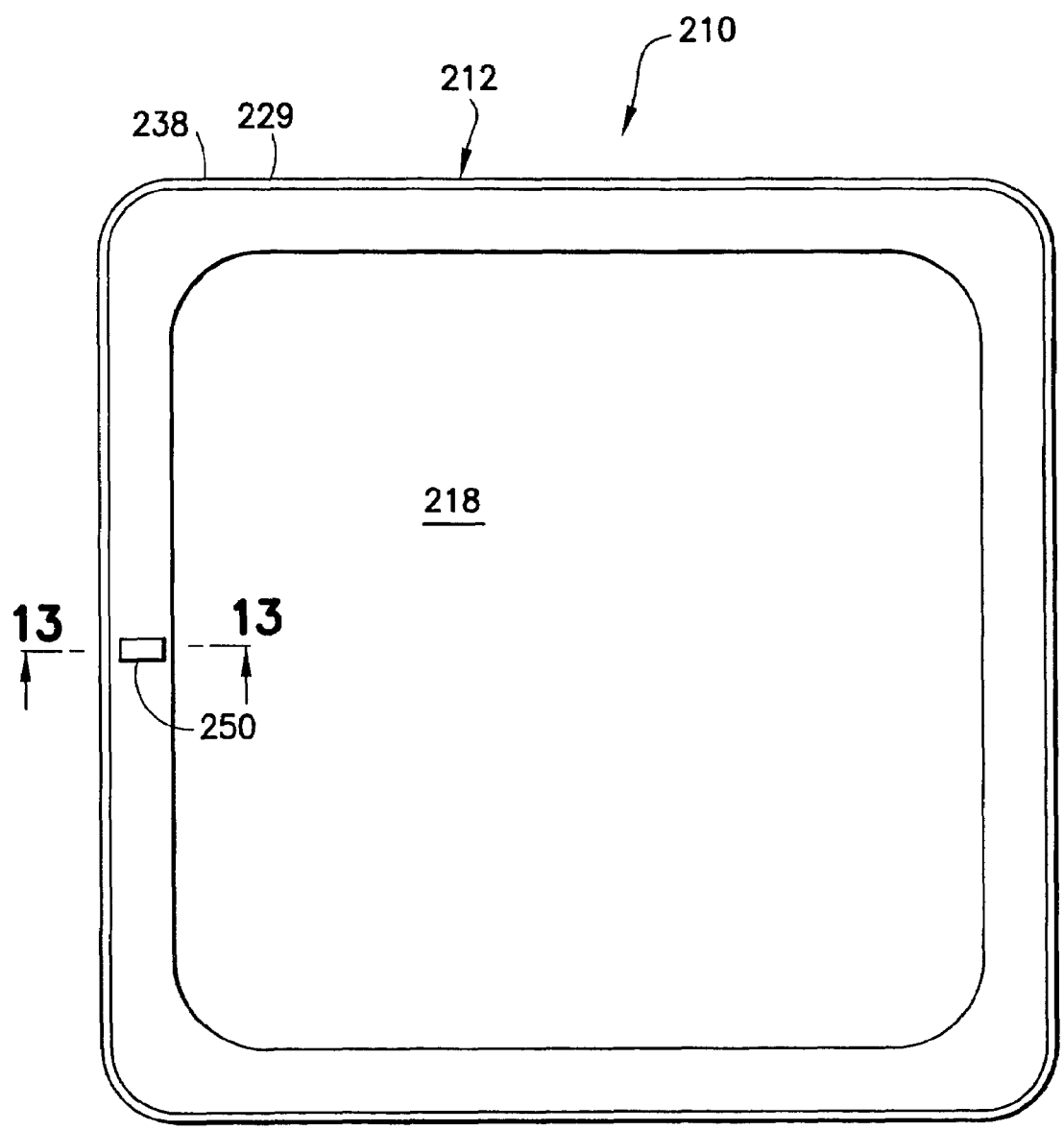
FIG. 12 is a top plan view of a third embodiment of the splash guard mounted in the culture dish depicted in the previous embodiments.
Figure 13:
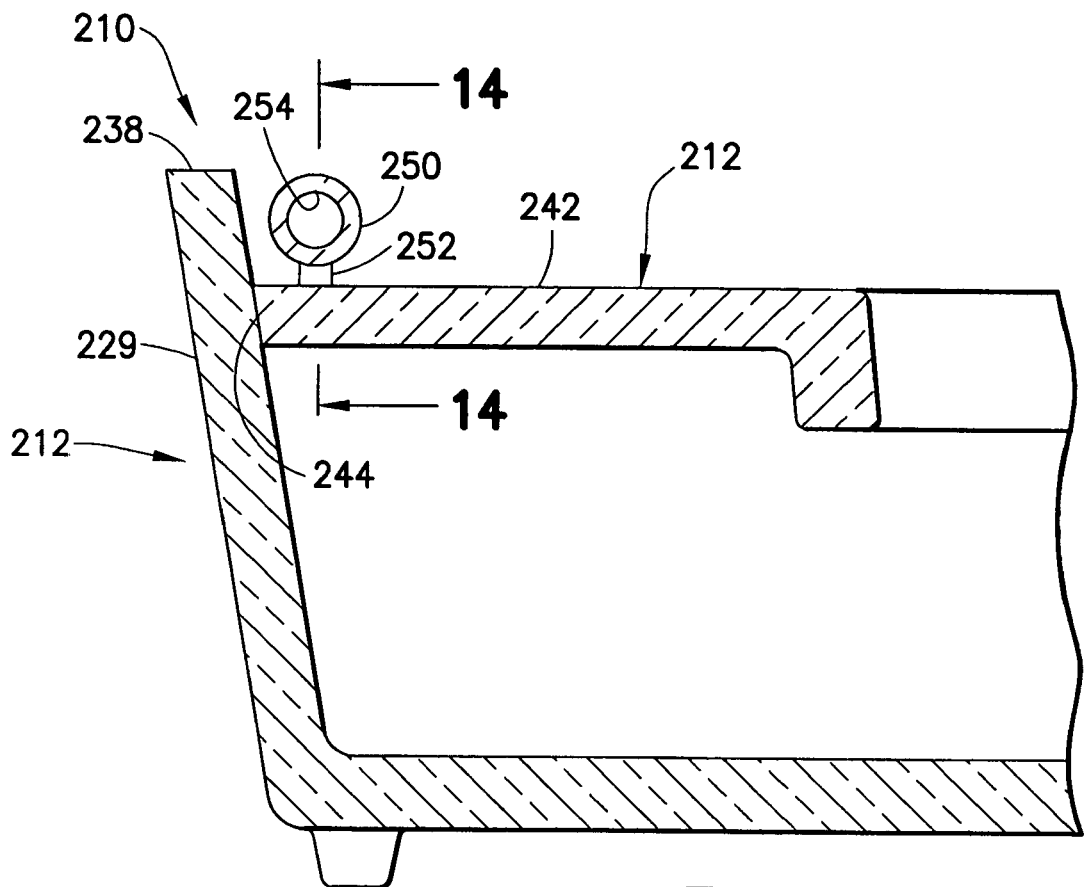
FIG. 13 is a cross-sectional view taken along line 12-12 in FIG. 12.
Figure 14:
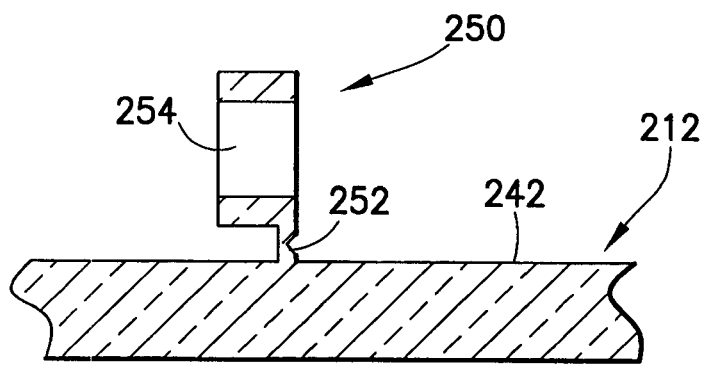
FIG. 14 is a cross-sectional view taken along line 13-13 in FIG. 13.
Figure 15:
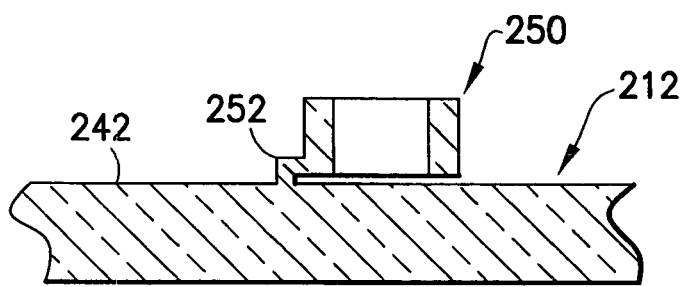
FIG. 15 is a cross-sectional view similar to FIG. 14, but showing the pull handle in a different rotational orientation.

Splash guard 214 further includes a pull handle 250 hingedly connected to a top surface of frame-shaped wall 242 by a living hinge 252. Pull handle 250 further includes an aperture 254 to facilitate digital or mechanical engagement with pull handle 250. Pull handle 250 can be rotated from a substantially upright orientation as shown in FIGS. 12-14 to a substantially prone orientation as shown in FIG. 15. Pull handle 250 can be gripped manually or by machine to lift splash guard 214 away from culture dish 212 to facilitate access to bottom wall 218. More particularly, pull handle 250 can be gripped between a thumb and forefinger so that splash guard 214 can be lifted up and away from culture dish 212. A cell scraper or other such tool then can be used easily to access biological cultures that have grown adjacent bottom wall 218. Pull handle 250 can be rotated into the prone orientation shown in FIG. 15 and will lie in a plane substantially flush with top edge 238 of side wall enclosure 229. A cover, such as cover 16 described above then can be placed on top edge 238 of side wall enclosure 229 to close culture dish assembly 210 while cultures are permitted to grow therein.

Figure 16:
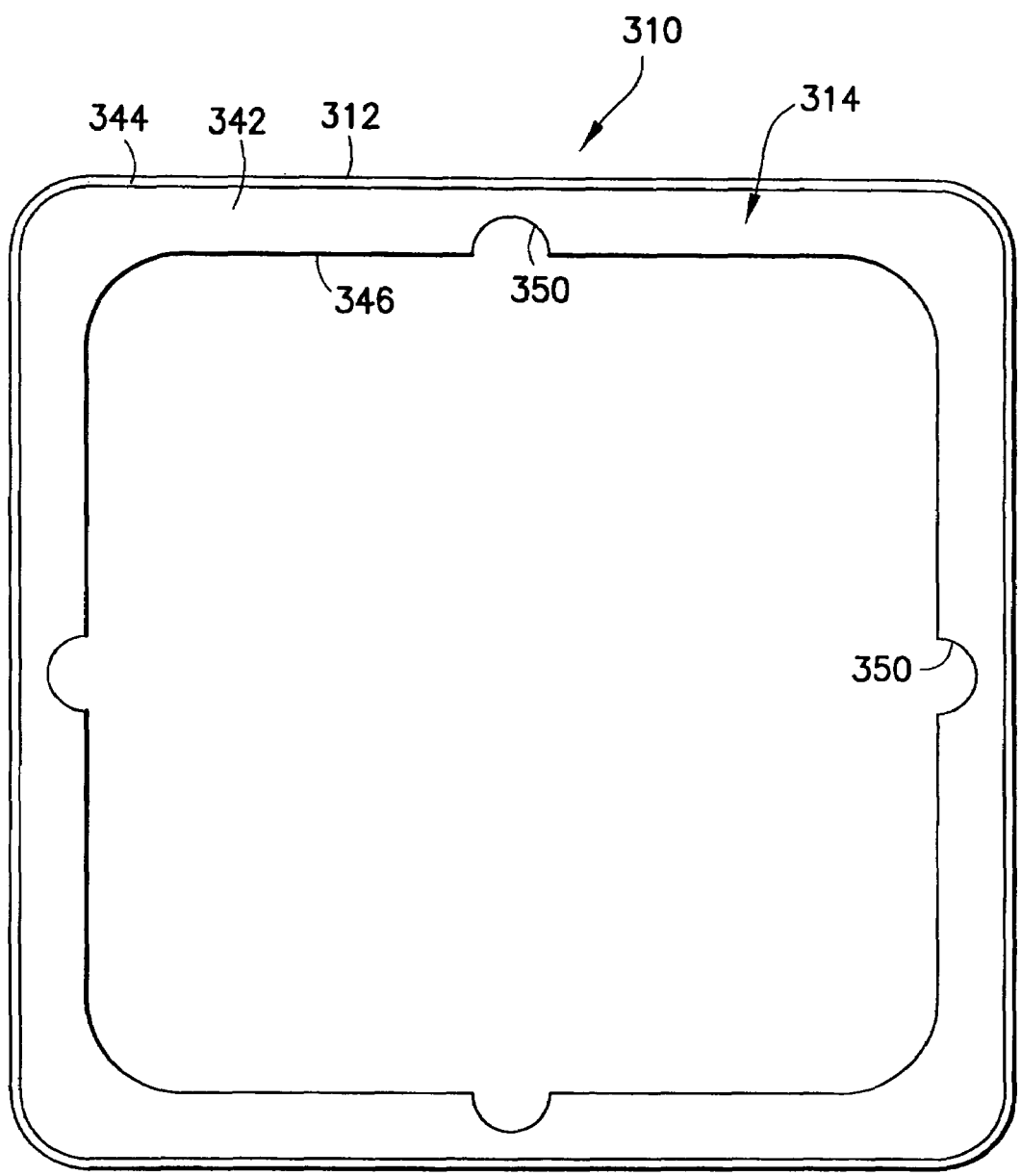
FIG. 16 is a top plan view of a fourth embodiment of the splash guard mounted in the above-described culture dish.

A fourth embodiment of a culture dish assembly in accordance with the subject invention is identified by the numeral 310 in FIG. 16. Culture dish assembly 310 includes a culture dish 312 that is substantially identical to culture dish 212 described above and illustrated in FIGS. 12 and 13. Culture dish assembly 310 further includes a splash guard 314 with a frame-shaped generally planar wall 342. Frame-shaped wall 342 has an outer periphery 344 and an inner periphery 346. Outer periphery 344 is dimensionally comparable to outer periphery 244 of splash guard 214 described above and illustrated in FIGS. 12-15. Inner periphery 346, however, is provided with a plurality of finger slots 350 that are dimensioned to be engaged by fingers or by laboratory equipment for pulling splash guard 314 out of culture dish 312.

Figure 17:
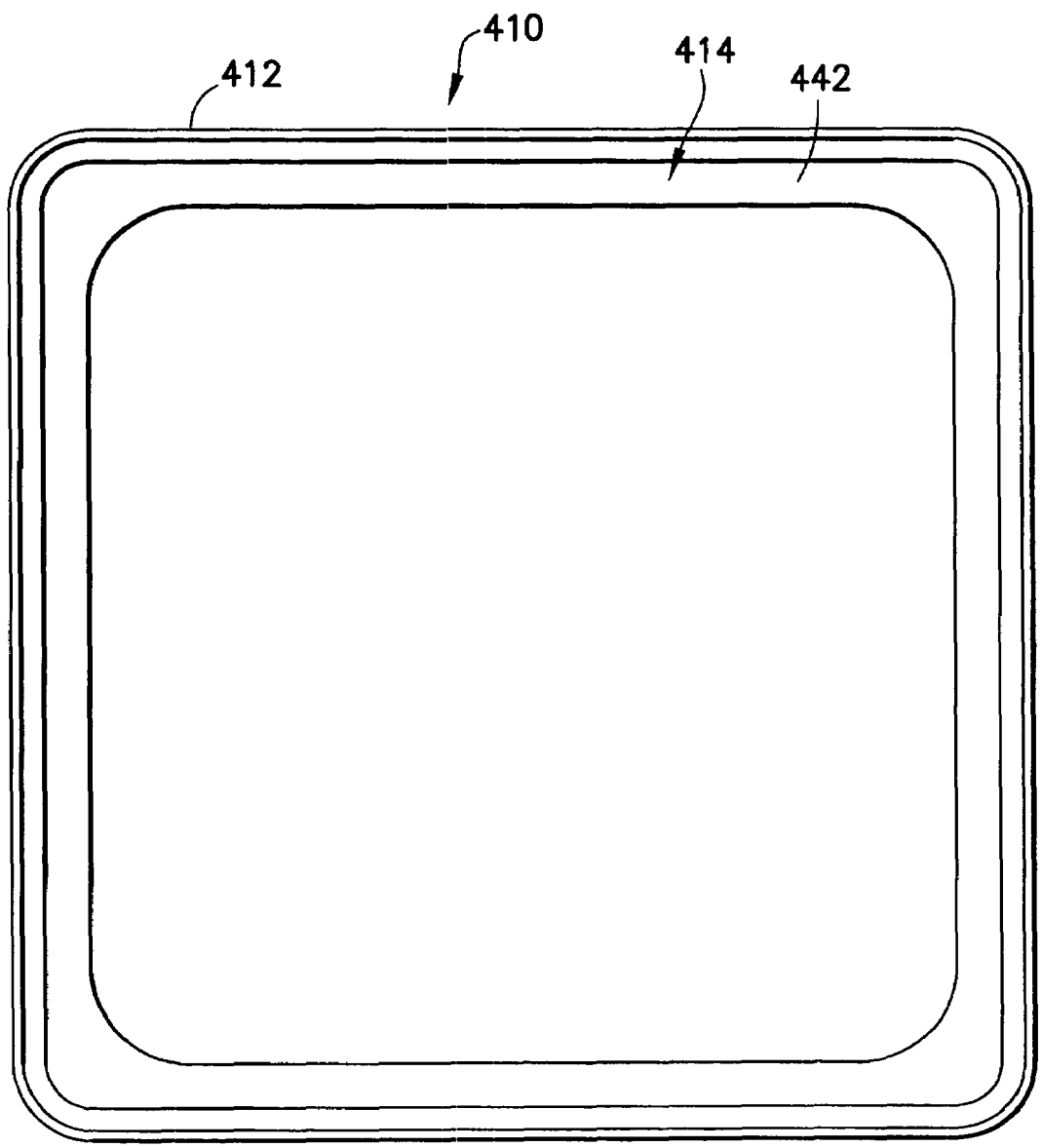
FIG. 17 is a top plan view of a fifth embodiment of the splash guard mounted in the above-described culture dish.
Figure 18:
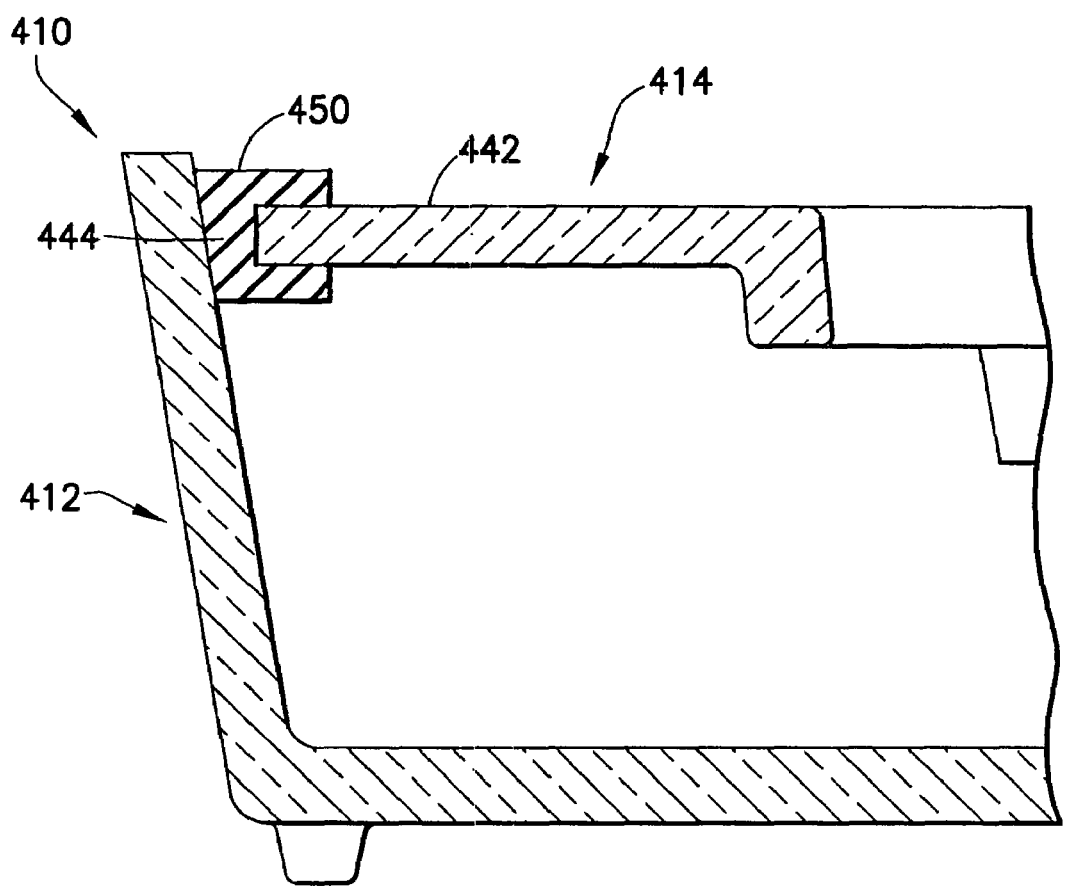
FIG. 18 is a cross-sectional view taken along lines 17-17 in FIG. 17.

A culture dish assembly in accordance with a fifth embodiment of the subject invention is identified generally by the numeral 410 in FIGS. 17 and 18. Culture dish assembly 410 includes culture dish 412 that is substantially identical to culture dish 212 described above and illustrated in FIGS. 12-15. Culture dish assembly 410 further includes a splash guard 414 with a substantially planar frame-shaped wall 442. Frame-shaped wall 442 includes an outer periphery 444 and an elastomeric gasket 450 mounted around outer periphery 444. Outer periphery 444 and gasket 450 are dimensioned to resiliently engage the inner peripheral surface of the sidewall enclosure on culture dish 412. Splash guard 414 may be provided with finger slots comparable to finger slots 350 shown in FIG. 16 or with a pull handle comparable to pull handle 250 shown in FIGS. 12-15.

What is claimed is:

1. A culture dish assembly comprising:

a culture dish having a polygonal bottom wall with an outer periphery and a side wall enclosure extending up from said bottom wall and having a top edge remote from said bottom wall, said side wall enclosure including a plurality of substantially planar panels and non-planar corners connecting adjacent panels, said side wall enclosure including a top edge spaced from said bottom wall, said side wall enclosure including a plurality of engagement structures formed on inwardly facing surface regions of said substantially planar panels at locations spaced from said non-planar corners, wherein said engagement structures comprise engagement structures formed on each of said planar panels of said side wall enclosure, wherein said engagement structures on said side wall enclosure are elongated and define a direction of elongation substantially parallel to said bottom wall of said culture dish, wherein said engagement structures on said side wall enclosure each are substantially rectangular, and, wherein said engagement structures on said side wall enclosure are projections that project inwardly relative to said side wall enclosure; and a splash guard having a frame-shaped top wall engaged on said top edge of said side wall enclosure and engagement flanges extending down from said top wall and nesting with, and interiorly of, portions of said planar panels, said engagement flanges including engagement structures releasably engaged with said engagement structures on said planar panels.

2. The culture dish assembly of claim 1, wherein said engagement structures on said splash guard are recesses dimensioned to closely engage said projections on said planar panels of said culture dish.

3. A culture dish assembly comprising:
a culture dish having a polygonal bottom wall with an outer periphery and a side wall enclosure extending up from said bottom wall and having a top edge remote from said bottom wall, said side wall enclosure including a plurality of substantially planar panels and non-planar corners connecting adjacent panels, said side wall enclosure including a top edge spaced from said bottom wall, said side wall enclosure including a plurality of engagement structures formed on inwardly facing surface regions of said substantially planar panels at locations spaced from said non-planar corners; and
a splash guard having a frame-shaped top wall engaged on said top edge of said side wall enclosure and engagement flanges extending down from said top wall and nesting with, and interiorly of, portions of said planar panels, said engagement flanges including engagement structures releasably engaged with said engagement structures on said planar panels, wherein said bottom wall of said culture dish defines a square with rounded corners.

4. A culture dish assembly comprising:
a culture dish having a polygonal bottom wall with an outer periphery and a side wall enclosure extending up from said bottom wall and having a top edge remote from said bottom wall, said side wall enclosure including a plurality of substantially planar panels and non-planar corners connecting adjacent panels, said side wall enclosure including a top edge spaced from said bottom wall, said side wall enclosure including a plurality of engagement structures formed on inwardly facing surface regions of said substantially planar panels at locations spaced from said non-planar corners; and
a splash guard having a frame-shaped top wall engaged on said top edge of said side wall enclosure and engagement flanges extending down from said top wall and nesting with, and interiorly of, portions of said planar panels, said engagement flanges including engagement structures releasably engaged with said engagement structures on said planar panels, wherein said top wall of said splash guard is substantially parallel to said bottom wall of said culture dish, and, wherein said top edge of said side wall enclosure defines an outer periphery, said top wall of said splash guard defining an outer periphery substantially registered with said outer periphery of said top edge of said side wall enclosure.

5. The culture dish assembly of claim 4, wherein said top wall of said splash guard further includes an inner periphery and an inner peripheral lip extending down from said inner periphery of said top wall toward said bottom wall.

6. The splash guard assembly of claim 4, wherein said top wall includes four corners, one of said corners being substantially concave for defining a pouring opening at said corner.

7. The culture dish assembly of claim 6, wherein said side wall enclosure tapers outwardly from said bottom wall to said top edge.

8. The culture dish assembly of claim 7, wherein said engagement flanges of said splash guard having outwardly facing surfaces that taper inwardly at further distances from said top wall of said splash guard.

9. A culture dish assembly comprising:
a culture dish having a polygonal bottom wall with an outer periphery and a side wall enclosure extending up from said bottom wall and having a top edge remote from said bottom wall, said side wall enclosure including a plurality of substantially planar panels and non-planar corners connecting adjacent panels, said side wall enclosure including a top edge spaced from said bottom wall, said side wall enclosure including a plurality of engagement structures formed on inwardly facing surface regions of said substantially planar panels at locations spaced from said non-planar corners; and
a splash guard having a frame-shaped top wall engaged on said top edge of said side wall enclosure and engagement flanges extending down from said top wall and nesting with, and interiorly of, portions of said planar panels, said engagement flanges including engagement structures releasably engaged with said engagement structures on said planar panels, wherein said frame-shaped top wall of said splash guard includes an inner periphery defining an opening for accessing said bottom wall of said culture dish, said culture dish assembly further comprising a cover removably mountable over said culture dish and said splash guard for at least substantially closing said opening defined by said inner periphery of said frame-shaped top wall of said splash guard.

10. The culture dish assembly of claim 9, wherein said splash guard further includes a plurality of breathing lugs projecting up from said top wall of said splash guard to permit gas exchange between said culture dish and areas surrounding said culture dish.

* * * * *